United States Patent [19]

Yamane et al.

[11] Patent Number: 4,533,637

[45] Date of Patent: Aug. 6, 1985

[54] CULTURE MEDIUM

[75] Inventors: Isao Yamane, No. 6-6-20, Minami, Yagiyama, Sendai-shi, Miyagi-ken; Mikio Kan, Sendai; Yoshiki Minamoto, Yokohama, all of Japan

[73] Assignees: Ajinomoto Co., Inc., Tokyo; Isao Yamane, Sendai, both of Japan

[21] Appl. No.: 379,369

[22] Filed: May 18, 1982

[30] Foreign Application Priority Data

May 28, 1981 [JP] Japan .................. 56-81600

[51] Int. Cl.$^3$ .......................... C12N 5/00; C12R 1/91
[52] U.S. Cl. ................................ 435/240; 435/948
[58] Field of Search .................. 435/240, 241, 948

[56] References Cited

U.S. PATENT DOCUMENTS

| | | | |
|---|---|---|---|
| 3,887,430 | 6/1975 | Torney et al. | 435/240 |
| 4,055,466 | 10/1977 | Torney et al. | 435/240 |
| 4,135,977 | 1/1979 | Horikoshi et al. | 435/97 |
| 4,198,479 | 4/1980 | Tytell et al. | 435/68 |
| 4,367,072 | 1/1983 | Vogtle et al. | 436/501 |
| 4,371,673 | 2/1983 | Pitha | 424/78 |

OTHER PUBLICATIONS

Yamane et al., "A-Cyclodextrin: A Partial Substitute for Bovine Serum Albumin in Serum Free Culture of Mammalian Cells" Cold Spring Harbor Conferences on Cell Proliferation, vol. 9, (1981), pp. 87–92.
Yamane et al., "A-Cyclodextrin, A Novel Substitute for Bovine Albumin in Serum Free Culture of Mammalian Cells" Proc. Jpn. Acad. Ser. B., (1981), 57(10), pp. 385–389, Chem. Abst., 96:100488r.
Yamane et al., "Role of Bovine Albumin in Serum Free Suspension Cell Culture Medium", Proc. Soc. Exp. Biol. Med., 149, (1975), pp. 439–442.
Ham et al., "Nutritional Requirements for Clonal Growth of Nontransformed Cells" in, Nutritional Requirements of Cultured Cells, (1978), p. 100.
Spector, "Fatty Acid Glyceride and Phospholipid Metabolism" in, Growth, Nutrition and Metabolism of Cells in Culture, (1972), pp. 257–275.
Toyama Chemical Company, "Vitamin E. and Cyclodextrin Inclusion Compounds" Jpn. Kokai Tokkyo Koho, 81/154,479, (4–1981), pp. 1–3, Chem. Abst., 96:103983.
Szejtli et al., "Enrichment of the Unsaturated Fatty Acid Content in Fatty Acid Mixtures by Formation of Inclusion Complexes" Hung. Teljes., 16,602, (1979), pp. 1–18, Chem. Abst., 92: 22061x.
Thoma et al., "Cycloamyloses" in Starch Chemistry and Technology by Wistler et al., (1965), pp. 215, 226–233, and 242–245.

Primary Examiner—Thomas G. Wiseman
Assistant Examiner—John Edward Tarcza
Attorney, Agent, or Firm—Oblon, Fisher, Spivak, McClelland & Maier

[57] ABSTRACT

On the new findings that cyclodextrin shows no cytotoxicity or only slight cytotoxicity on cell growth and that lipophilic substances such as unsaturated fatty acids and lipophilic vitamins when present together with, or included in, cyclodextrin show such effects as cell growth promoting effect and accelerating effect of the productivity of valuable products, a serum-free or serum-reduced culture medium or a substitute composition for serum for a culture medium comprising a cyclodextrin and at least one lipophilic nutrient substance, said cyclodextrin and said lipophilic nutrient substance being preferably in the form of inclusion complex between them, is provided.

19 Claims, 6 Drawing Figures

CULTURE MEDIUM

DETAILED EXPLANATION OF THE INVENTION

This invention relates to some improvements in culture media, in which a serum-free culture medium may be provided, a substitute composition for serum for culture media may be provided, the serum concentration or the serum moiety in a culture medium for mammalian cells may be reduced, or better use may be made of the serum moiety contained in a culture medium.

So far, culture media for the proliferation of mammalian cells generally have been prepared by adding a large amount of serum and, therefore, conventional culture media usually contain a large amount of serum. In connection with such culture media, the following problems are pointed out, for example:

(a) For the production of interferons by human cells, or for the propagation of virus in order to prepare vaccine, for example, fetal bovine serum or calf serum is usually added in amounts of around 10% to these culture media. Therefore, more than half of the cost of such media is usually occupied by such sera, and these media will be expensive.

(b) In addition, there is the troublesome necessity of checking serum lots in advance before the sera are used to prepare culture media, because these sera might be contaminated with mycoplasma or virus, and because the quality of these sera may, vary from lot to lot.

(c) Further, these sera contain various and unidentified proteins derived from bovines or horses, which make it difficult to isolate such products as interferon from the remainder of the culture medium.

The inventors had tried to decrease the serum concentration in a culture medium or to develop serum-free culture media, and found that serum albumin may substitute for sera and that mammalian cells grow as well in a culture medium containing serum albumin without any other serum components as in conventional serum-containing culture media. The inventors have filed a patent application for an invention based on these findings. See Japanese patent application No. 149,731/1980.

The inventors further tried to develop another serum-free culture medium, which is easier to prepare or handle and is less expensive accordingly.

There were finally successful in preparing a new serum-free culture medium which contains a cyclodextrin and a lipophilic substance at the same time or a cyclodextrin-lipophilic substance inclusion compound.

This new serum-free culture medium has been found to allow mammalian cells to grow without using any serum albumin or serum as usually employed in a conventional serum-containg medium, or a known serum-free culture medium.

Furthermore, water-insoluble or sparingly soluble unsaturated or saturated fatty acids and other water-insoluble or sparingly soluble nutrients have been very difficult to add to culture media without cytotoxic effect.

The inventors were first successful in introducing these lipophilic nutrients into a serum-free culture medium by using a cyclodextrin as vehicle. This invention was established by finding the fact that a cyclodextrin is not cytotoxic or only slightly cytotoxic for mammalian cell growth and also that such a compound is an appropriate additive to introduce various lipophilic substances such as saturated or unsaturated fatty acids and lipophilic vitamins. In other words, use of a cyclodextrin makes it easy to add lipophilic nutrients to a serum-free culture medium.

There are three cyclodextrins, i.e., $\alpha$-, $\beta$-, and $\gamma$-cyclodextrins, and all the cyclodextrins are employable in this invention. Among them, $\alpha$-cyclodextrin is the best for the purpose of this invention because of its non-cytotoxicity against mammalian cell growth. $\beta$-Cyclodextrin is generally employed as drug preparation, but shows some cytotoxic effect on the growth of mammalian cells. Therefore, $\beta$-cyclodextrin is not as good as $\alpha$-cyclodextrin for that purpose at its higher concentrations. See FIG. 6.

In this invention, cyclodextrin is used to include lipophilic substances to be added as nutrients in a culture medium or to decrease the cytotoxicity of such ingredients against mammalian cells.

The lipophilic substances encompassed by this invention include unsaturated fatty acids such as linoleic acid, linolenic acid, oleic acid, arachidonic acid and erucic acid and their glycerides, saturated fatty acids such as palmitic acid and stearic acid and their glycerides, and lipophilic vitamins such as vitamins A, D and E.

A cyclodextrin or lipophilic substance may be added as it is (i.e., as such), or a mixture of a cyclodextrin and a lipophilic substance may be added. A cyclodextrin and lipophilic substance are preferably added to a culture medium after they are reacted with one another.

The reaction is, for example, carried out, as follows; a cyclodextrin aqueous solution and a solution of lipophilic substance dissolved in a hydrophilic organic solvent such as an alcohol or dioxane are first prepared, then both solutions are mixed and, for example, heated up to 75° C. or heated to 70° C. and kept at this temperature for 5 minutes. The reaction product thus formed is preferably introduced into the remainder of a culture medium after it is separated from the remainder of the reaction mixture. The reaction product is, for example, precipitated by cooling the reaction mixture and it is easily separated in such precipitate form from the remainder of the reaction mixture.

The reaction product is usually in the form of an inclusion complex in which the cyclodextrin surrounds the lipophilic substance, but it may be in a form in which cyclodextrin is bound to the lipophilic substance in some other way.

The amount of cyclodextrin to be used depends on the purposes of its use. When it is used in the form of its inclusion complex with a lipophilic substance, an inclusion complex is preferably used which results from reacting cyclodextrin with a lipophilic substance in a cyclodextrin/lipophilic substance molar ratio of 3~500:1, and usually 10~100:1.

For the preparation of culture medium for mammalian cells, the addition of serum has been thought to be essential. A serum-free culture medium of Japanese patent application No. 149,731/1980 does not require serum as such, but still requires serum albumin, one component of serum.

Figure 1:
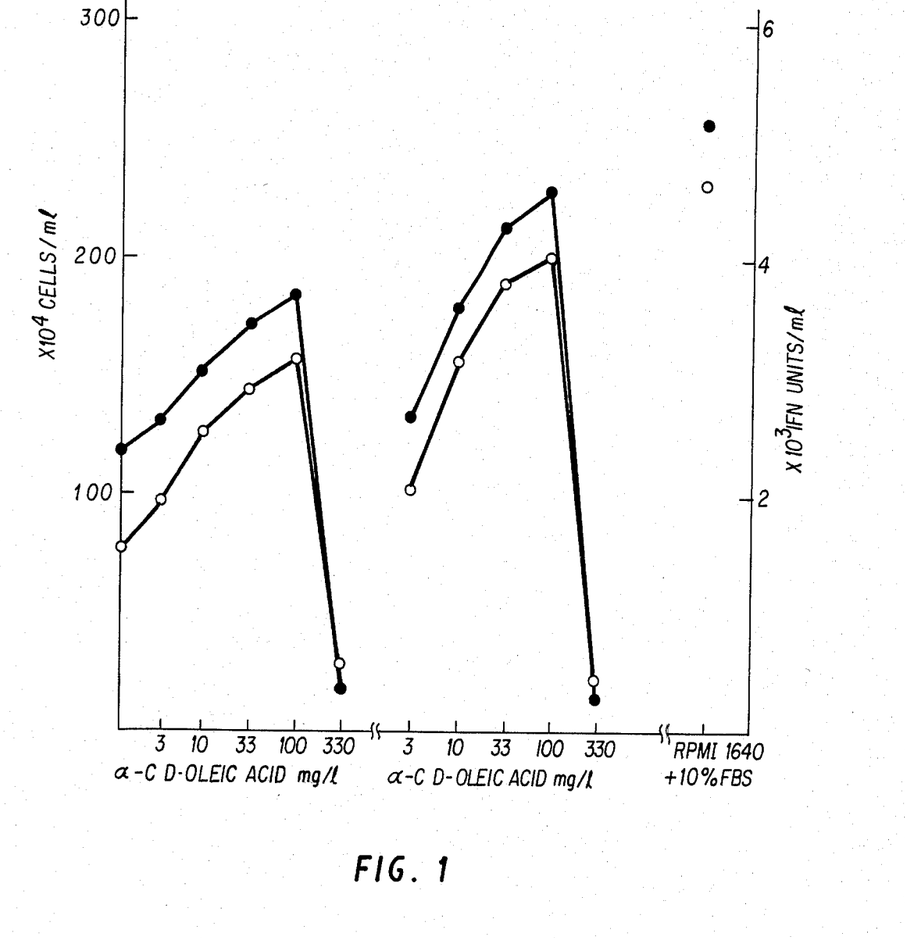

However, according to this invention, for example, in a serum-free culture medium which contains a reaction product of linoleic acid with $\alpha$-cyclodextrin instead of serum or serum albumin, mammalian cells can grow as well as in a conventional serum-containing medium and can produce physiologically active substances such as interferon. See. FIG. 1.

Figure 2:
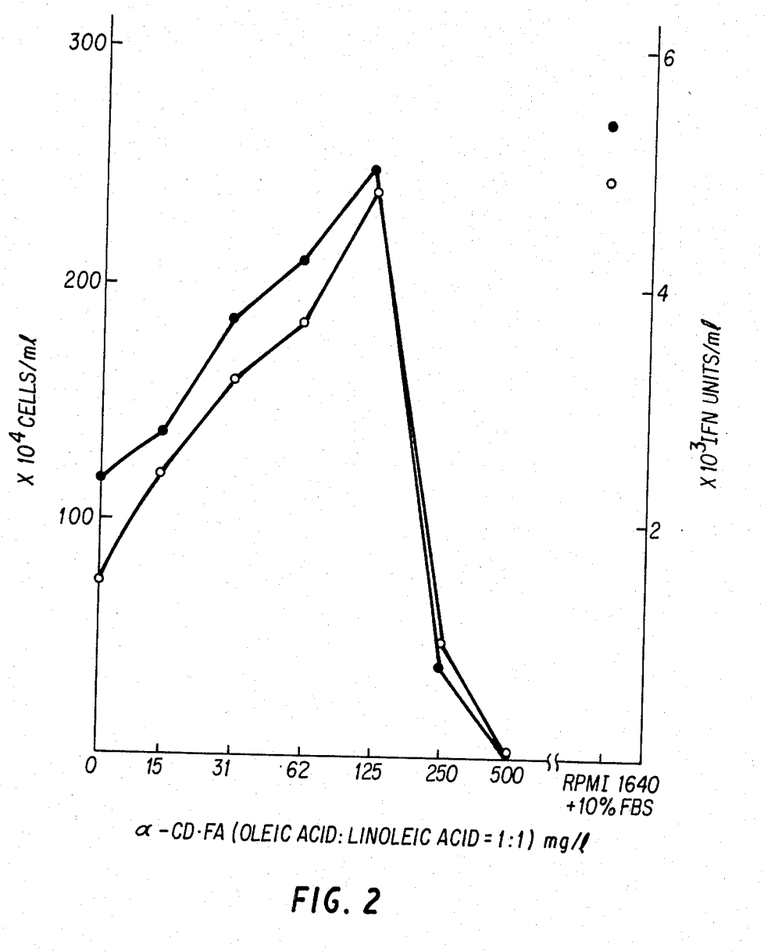
Figure 3:
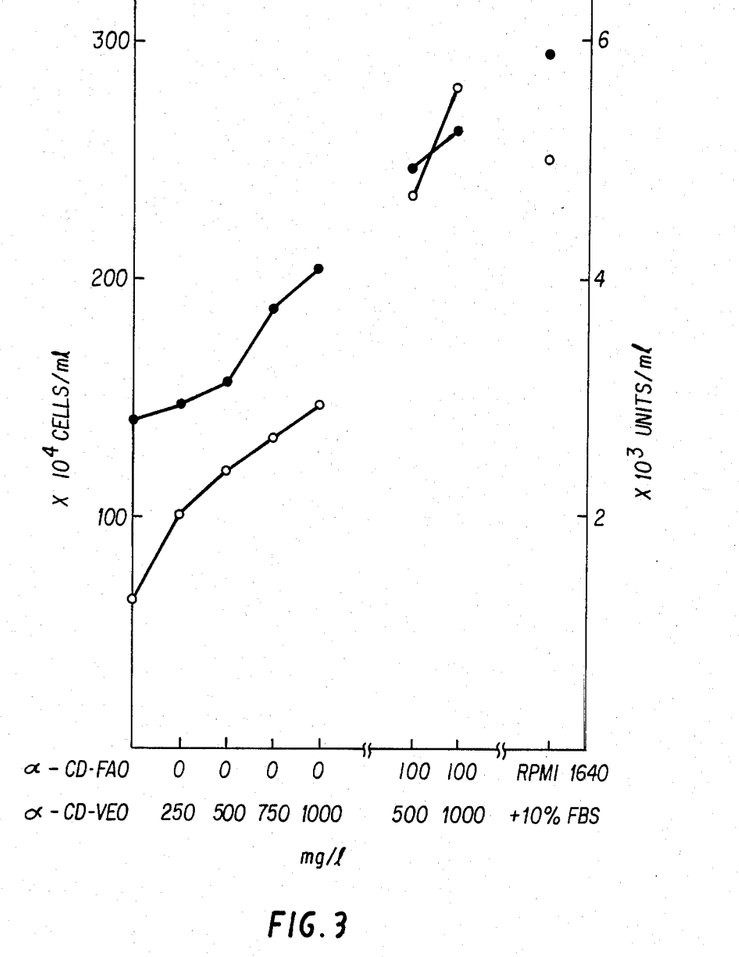

Cell growth and production of a physiologically active substance can further be improved when other unsaturated fatty acids such as oleic acid and linolenic acid, and/or vitamin E are added as their respective inclusion complexes with cyclodextrin, together with the linoleic acid/cyclodextrin inclusion complex. See FIGS. 2, 3 and 5. An inclusion complex prepared from vitamin E and a cyclodextrin, even when singly used, can also improve cell growth or enhance productivity of interferon. See. FIG. 3. So can an inclusion complex of a cyclodextrin with one of the other unsaturated fatty acids such as oleic acid. See FIG. 1.

When an inclusion complex prepared under the above-mentioned conditions from linoleic acid and α-cyclodextrin is used as the substitute for serum or serum albumin, it is introduced in amounts of about 0.1~5 mg per liter of culture medium, preferably 0.5~2 mg per liter of culture medium, expressed in terms of the linoleic acid moiety. Usually, larger amounts of the linoleic acid moiety than the above will have an evil effect on cell growth, i.e., cytotoxicity. The lower limit concentration of the linoleic acid moiety which will have the cytotoxic effects on cell growth will, however, be increased up to 10 mg per liter of culture medium, if additionally α-cyclodextrin is added into the medium in amounts of 300~1000 mg per liter of culture medium. See FIG. 4.

An inclusion complex of α-cyclodextrin with other fatty acids than linoleic acid, such as oleic acid, linolenic acid, palmytic acid and stearic acid, is preferably introduced in amounts of around 0.1~1 mg/l expressed in terms of the fatty acid moiety.

When the inclusion complex prepared from vitamin E and α-cyclodextrin is added to the remainder of a serum-free or serum albumin-free culture medium, its optimal concentration is around 0.5~10 mg/l, preferably 1~5 mg/l, as expressed in terms of the concentration of vitamin E.

A serum- or serum albumin-free culture medium according to this invention contains as other ingredients cell growth factors such as insulin and human transferrin, and nucleic acid precursors such as hypoxanthine, thymidine, deoxyadenosine, and deoxycytidine, together with such carbon sources as glucose, amino acids, vitamins, minerals and other nutrients which are contained in a conventional serum-supplemented medium or a known serium-free medium for mammalian cell culture.

A cell growth factor is preferably used in a concentration of around 1~100 mg per liter of culture medium, and a nucleic acid precursor is preferably used in a concentration of around 0.01~50 mg per liter of culture medium. Two or more cell growth factors may be used simultaneously, depending on the kind of mammalian cells, as may two or more nucleic acid precursors.

Glucose is usually employed as the carbon source in amounts of 0.5~10 g per liter of culture medium. Other carbon sources such as pyruvate may also be used.

Amino acids such as L-alanine, L-arginine, L-glutamine, L-methionine, L-threonine, L-lysine, L-valine, and L-phenylalanine are also used, such amino acids being the components of protein. Into a serum-containing culture medium, essential amino acids are mainly introduced, but various non-essential amino acids as well as essential amino acids are preferably introduced into a serum-free culture medium according to this invention. Amino acids are preferably added in total amounts of around 0.5~5 g per liter of culture medium.

Other amino acids are preferably supplemented, in consideration of usual serum-containing media.

Vitamins such as ascorbic acid, riboflavin, thiamine.HCl, Ca-pantothenate, nicotic acid amide, pyridoxal.HCl, i-inositol, folic acid, vitamin $B_{12}$, and biotin are added, together with minerals such as NaCl, KCl, $CaCl_2$, $MgSO_4$, $NaH_2PO_4$, $ZnSO_4$, and $NaSeO_3$, in adequate amounts.

In addition, such metabolic intermediates as choline bitartrate, glutathione and putrescine.2HCl, and buffering substances such as $NaHCO_3$, β-glycerophosphate.2Na, and/or N-2-hydroxyethylpiperazine-N-2-ethane sulfonate are adequately supplemented.

In addition to the above ingredients and additives, the following basal media are referred to, in determining the composition of a culture medium addording to this invention; Dulbecco's Modified Eagle Medium, RPMI-1640 Medium, Eagle Minimum Essential Medium and Ham F-12 Medium.

The method of preparing a culture medium addording to this invention is not critical. It may be prepared, for example, by dissolving all the ingredients and additives in water in their respective appropriate concentrations first and then filtering the solution on a membrane filter under pressure to get a sterilized culture medium. It would be apparent from the above disclosure that a cyclodextrin and a lipophilic substance are preferably used in the form of an inclusion complex between them.

Mammalian cells which can grow in a serum-free culture medium of this invention are not limited to specified cells, but a wide variety of cells such as lymphocytes, fibroblastes, epithelial cells, and their transformed cells, various neoplastic cells, and hybridomas derived therefrom can grow therein.

Examples of such mammalian cells include Epstein-Barr Virus (EBV)-transformed human lymphoblastoid cell lines such as UMCL and C5180Y, human Burkitt's lymphoma-derived Namalwa cells, murine lymphoid cell-derived myeloma SPI cells, human fibroblast cells such as HEL and IMR-90, human tumor-derived epithelial cells such as HeLa-$S_3$, Hep-2 and KB, human primary cultured cells, rat Yoshida sarcoma cells, hamster fibroblast cells BHK-21, murine fibroblast cells 3T3, and murine lymphoma cells YAC-1.

The method of culturing mammalian cells with the use of a culture medium of this invention is not critical, either. Mammalian cells are cultured in a serum-free culture medium of this invention under the same or almost the same conditions as those for a conventional serum-containing medium; for example, cells are cultured in a culture medium at a initial cell density of $10^4 \sim 10^6$ cells/ml and 35°~37° C. while supplying 4~6% (v/v) $CO_2$-containing sterilized air into the culture vessel. Fibro-blast cells are preferably cultured under lower $O_2$ supply (5~10% v/v) than a normal atomosphere, especially in a serum-free medium.

Serum-free media of this invention are employable not only for the cell growth of mammalian cells but also for the production of useful physiologically active substances such as interferons, lymphokines, and antibodies.

Serum-free media of this invention have been established on the basis of the inventors' findings that a cyclodextrin does not show any cytotoxic effect on cell growth and that lipophilic substances included in a cyclodextrin still show such effects as cell growth promoting effect and accelerating effect of the productivity of valuable products. This invention has also been established on the finding that the solubility and stability in water of the culture medium ingredients are improved by including them in a cyclodextrin as a vehicle.

In accordance with this invention, those substances which are water-insoluble, unstable in culture medium or cytotoxic as such and which were accordingly considered as being unemployable as culture medium ingredients have been made available. In other words, this invention will enlarge the availability of various ingredients and the ranges of researches on the developments of new culture media.

It would be apparent from the foregoing disclosure, especially in connection with the way that cyclodextrin has effects on cell growth and/or some culture medium ingredients, that a conventional serum culture medium may be made more effective when it is added with cyclodextrin because some lipophilic substances originating from serum are contained in such a conventional medium. A culture medium containing serum albumin at its lower concentrations instead of serum may also be made more effective a cyclodextrin is added because commercial serum albumin products such as crystalline albumin and Cohn's Fraction V are usually accompanied by lipophilic substances. An animal cell culture medium comprising cyclodextrin as well as ordinary nutrients and additives including serum or serum albumin is accordingly in accordance with this invention.

It would also be very apparent that the serum moiety or the serum albumin moiety in a conventional serum culture medium may be partially replaced with at least one lipophilic nutrient and cyclodextrin, said lipophilic substance and cyclodextrin being preferably in the form of an inclusion complex between them. A conventional animal cell culture medium in which the serum moiety or the serum albumin moiety is partially replaced with at least one lipophilic substance nutrient and cyclodextrin is also in accordance with this invention.

An animal cell culture nutrient substitute composition for serum comprising at least one lipophilic substance nutrient and cyclodextrin may be put on the market as such and it is also in accordance with this invention.

Take a lipid as ingredient, for example, linoleic acid. Linoleic acid shows almost no growth promoting effects at a concentration lower than 1 mg/l when linoleic acid itself is directly added in a culture medium, while at a concentration more than 1 mg/l this fatty acid shows cytotoxic effect on the cell growth. However, if it is added in the form of its inclusion complex with α-cyclodextrin into a culture medium, the upper limit of the fatty acid concentration which shows cytotoxicity is increased to 10 mg per liter of culture medium and at a lower concentration than this concentration, mammalian cells grow well and produce sufficient amounts of physiologically active substances, such as interferon.

Based on these new findings, the inventors have been successful in dispensing with, or reducing, serum which had been essential for the cell growth but was very expensive and appeared to be difficult to obtain, and established a new culture medium which contains no, or at least less, proteinaceous substances. At the same time the inventors opened the way to sterilize culture medium by autoclave. Use of a culture medium of this invention makes it easier to isolate and purify the product accumulated in the culture medium. Mass production of culture media is also made easier, according to this invention.

It is necessary to add serum albumin or an expensive cell-attachment factor such as fibronectin to the medium when fibroblast cells are cultivated in ordinary serum albumin-containing medium. No fibronectin, however, needs to be added if an inclusion complex prepared from α-cyclodextrin and an unsaturated fatty acid such as linoleic acid is added to the medium.

Further, there have not been known any good means of introducing lipophilic vitamins such as vitamin E into a culture medium without an organic solvent, though such vitamins have been considered as essential for cell growth, but now these nutrients may be added in sufficient amounts into a culture medium according to this invention.

This invention will be explained in greater detail with reference to the following examples.

Interferon activity produced was determined in terms of anti-viral activity using FL cells and Vesicular Stomatitis Virus in the following examples.

EXAMPLE 1 (Propagation of UMCL cells)

Fresh heparinized umbilical cord blood, 20 ml, was obtained from a new-born infant. Then the cord blood lymphocytes were quickly isolated by the Ficoll isopaque density gradient method. The cord blood lymphocyte fraction was mixed with 3 times the volume of Eagle's Minimum Essential Medium (Nissui Pharmatheutical Co.) and the mixture was centrifuged. The supernatant was discarded. After repeating this treatment 3 times, the washed lymphocytes were suspended at a cell density of $3 \times 10^6$/ml in Culture Medium RPMI-1640 (Nissui Pharmatheutical Co.) containing 10 v/v % fetal bovine serum.

To this lymphocytes suspension, EBV (Epstein Barr Virus) grown in the B-95-8 cells was added in a concentration of $5 \times 10^5$ $TD_{50}$/ml, and this mixture was incubated at 37° C. for 2 hours, followed by harvesting the lymphocytes with a centrifuge. After washing these lymphocytes with Eagle's MEM medium 3 times, the lymphocytes were resuspended at a cell density of $3 \sim 10^6$/ml in Culture Medium RPMI-1640 containing 10 v/v % fetal bovine serum and cultured at 36°~37° C. for 1.5 months in a humidified atmosphere containing 5% $CO_2$ in air. During this cultivation, fresh RPMI-1640 medium containing 10 v/v % fetal bovine serum was added in an equal volume, or a half volume of the culture medium medium was exchanged with this fresh medium every 5 days.

Two additional samples of umbilical cord blood from newborn infants were processed in the same way and 3 samples (in total) of lymphoblastoid cells, i.e., UMCL-1, UMCL-2 and UMCL-3, were prepared.

The spontaneous interferon productivity of these transformed cells was assayed and the results are shown in Table 1.

The assay was carried out as follows; Each lymphoblastoid cell line was cultured at an initial cell density of $5 \times 10^5$/ml in Culture Medium RPMI-1640 containing 10 v/v % fetal bovine serum at 37° C. for 5 days in a humidified atmosphere containing 5% $CO_2$ in air and the interferon activity in the supernatant was measured.

TABLE 1

| Cell Line | Interferon Activity |
| --- | --- |
| UMCL-1 | 2.5 ($10^3$ U/ml) |
| UMCL-2 | 6.1 |
| UMCL-3 | 4.5 |

In connection with this example, reference is made to T. Sato et al., Exp. Cell Res., 138, 127 (1982).

EXAMPLE 2

A culture medium named RITC 56-1 was prepared by dissolving in a Dulbecco's Modified Eagle Medium having the composition shown under A the additional nutrients and additives in the given amounts shown under B.

| A (Dulbecco's Modified Eagle Medium): | |
|---|---|
| NaCl | 6400.0 (mg/l) |
| KCl | 400.0 |
| $CaCl_2$ (non-hydrate) | 200.0 |
| $MgSO_4$ (non-hydrate) | 97.7 |
| $NaH_2PO_4.2H_2O$ | 125.0 |
| $Fe(NO_3)_3.9H_2O$ | 0.1 |
| Glucose | 1000.0 |
| Na pyruvate | 110.0 |
| L-arginine.HCl | 84.0 |
| L-Cystine.2HCl | 62.6 |
| glycine | 30.0 |
| L-glutamine | 584.0 |
| L-histidine.HCl.$H_2O$ | 42.0 |
| L-isoleucine | 104.8 (mg/l) |
| L-leucine | 104.8 |
| L-lysine.HCl | 146.2 |
| L-Methionine | 30.0 |
| L-phenylalanine | 66.0 |
| L-serine | 42.0 |
| L-threonine | 95.2 |
| L-tryptophan | 16.0 |
| L-tyrosinate.2Na | 89.5 |
| L-valine | 93.6 |
| choline bitartrate | 7.2 |
| folic acid | 4.0 |
| nicotinic acid amide | 4.0 |
| Ca pantothenate | 4.0 |
| pyridoxal.HCl | 4.0 |
| riboflavin | 0.4 |
| thiamine.HCl | 4.0 |
| i-inositol | 7.2 |
| Phenol Red | 5.0 |
| B (Additional Nutrients): | |
| insulin | 10 (mg/l) |
| human transferrin | 5 |
| hypoxanthine | 4 |
| thymidine | 0.7 |
| deoxycytidine | 0.03 |
| deoxyadenosine | 1.0 (mg/l) |
| 6.8-dihydroxypurine | 0.3 |
| glucose | 1000 |
| mannose | 500 |
| galactose | 500 |
| lecithin | 2.5 |
| cholesterol | 1 |
| L-alanine | 20 |
| L-asparagine.$H_2O$ | 56 |
| L-aspartic acid | 20 |
| L-cysteine.HCl.$H_2O$ | 40 |
| L-glutamic acid | 20 |
| L-proline | 20 |
| ascorbic acid | 10 |
| biotin | 0.2 |
| folinic acid | 0.01 |
| vitamin $B_{12}$ | 0.1 |
| $FeSO_4.7H_2O$ | 0.8 |
| $ZnSO_4.7H_2O$ | 0.02 |
| $Na_2SeO_3$ | 0.004 |
| $CaCl_2$ | 100 |
| glutathione | 1.0 |
| putrescine.2HCl | 0.1 |
| $\beta$-glycerophosphate.2Na | 1500 |
| $NaHCO_3$ | 1300 |

On the other hand, the inclusion complex between $\alpha$-cyclodextrin ($\alpha$-CD) and linoleic acid, oleic acid or vitamin E (VE) was prepared as follows;

1 mg of $\alpha$-CD was dissolved in 7 ml of distilled water, and 10 mg of linoleic acid, oleic acid or vitamin E was dissolved in 7 ml of ethanol. Both the aqueous and ethanolic solutions were mixed and the mixture was heated to, and kept at, 70° C. under bubbling with nitrogen gas until the mixture became opalescent. The opalescent solution was immediately left at room temperature, and then kept at 4° C. for additional 20 hrs after it had cooled to the room temperature. The precipitate formed, i.e., inclusion complex, was collected by centrifuging, lightly washed once with 10 ml of ethanol and dried in vaccuo. The resulting powder was washed two times with petroleum-ether and dried in vaccuo.

Figure 4:
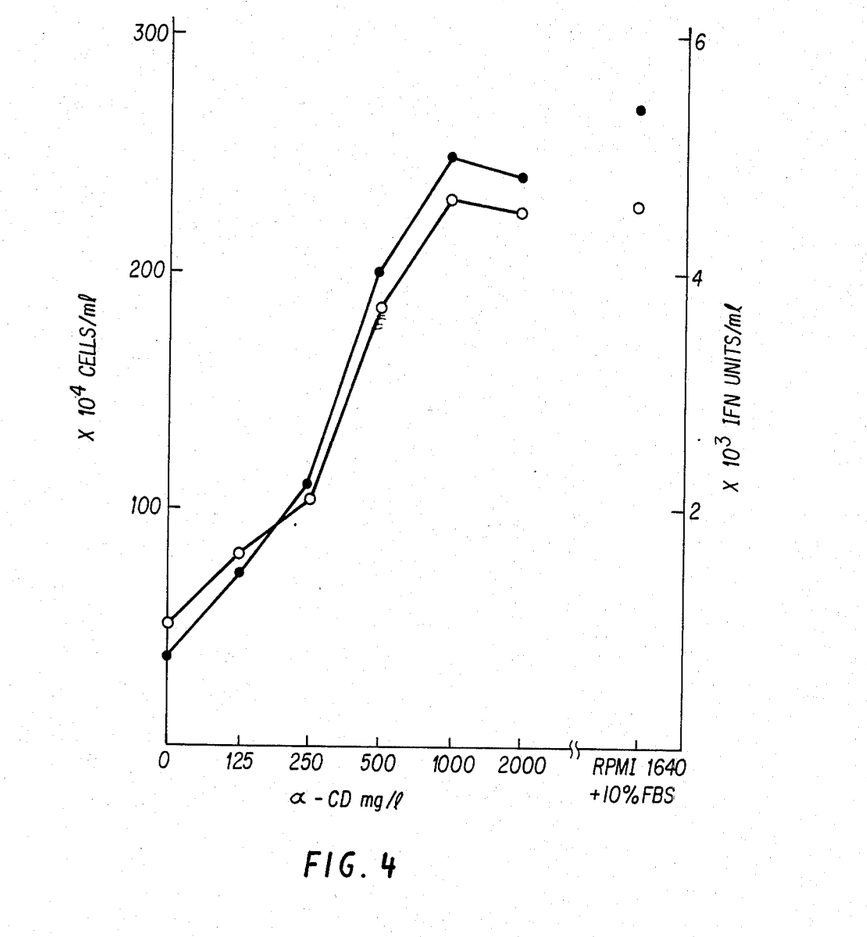

FIGS. 1~4 show the cell density and interferon production in the cultured medium when an UMCL-3 cell line was cultured in the RITC 56-1 culture medium supplemented with one or more inclusion complexes (FIGS. 1~3) and further with $\alpha$-cyclodextrin (FIG. 4).

The procedures are as follows;

RITC 56-1 culture medium was supplemented with one or more inclusion complex and further $\alpha$-cyclodextrin, as the case may be, as shown in FIGS. 1~4 in the respective amounts given in the same figures. The resulting solution was sterilized by filtering with a membrane filter. In the resulting medium UMCL-3 cells were inoculated at an initial cell density of $5 \times 10^5$ cells/ml, and cultured for 5 days at 37° C. under 5% $CO_2$-95% air. The cell density and interferon production in the cultured medium were measured.

In connection with FIG. 4, the culture media were RITC 56-1 culture media supplemented with 300 mg/l of the inclusion complex of $\alpha$-cyclodextrin with linoleic acid and further with $\alpha$-cyclodextrin in the amounts given in the figure.

The same cell line was cultured in RPMI-1640 culture medium supplemented with 10 v/v % fetal bovine serum, and the results are shown on the right side in all the figures for the purpose of comparison.

In all the figures, the closed circles and open circles indicate the concentrations of viable cells and interferon production, respectively.

EXAMPLE 3

A culture medium named RITC 80-7 was prepared by using an MEM medium and some other nutrients and additives.

The composition of the RITC 80-7 medium is as follows;

| MEM medium | 9400 (mg/l) |
|---|---|
| (Nissui Pharmatheutical Co.) | |
| L-aspartic acid | 13.3 |
| L-glutamine | 292 |
| glycine | 7.5 |
| L-glutamic acid | 0.15 (mg/l) |
| L-proline | 3.5 |
| L-serine | 10.5 |
| folinic acid | 0.00005 |
| 3,3',5-triiodo-L-thyronine | 0.0002 |
| mouse-EGF | 0.01 |
| human transferrin | 10 |
| insulin | 1 |
| vitamin $B_{12}$ | 0.02 |
| biotin | 0.02 |
| putrescine.2HCl | 0.02 |
| Na pyruvate | 110 |
| Choline chloride | 16 |
| thymidine | 0.07 |
| hypoxanthine | 0.24 |
| $CuSO_4.5H_2O$ | 0.0000025 |
| $FeSO_4.7H_2O$ | 0.8 |
| $MnSO_4.7H_2O$ | 0.0000024 |
| $(NH_4)_6Mo_7O_{24}.H_2O$ | 0.0012 |

| -continued | |
|---|---|
| NiCl$_2$.6H$_2$O | 0.000012 |
| NH$_4$VO$_3$ | 0.000058 |
| H$_2$SeO$_3$ | 0.00039 |
| N—2-hydroxyethylpiperazine-N—2-ethane sulfonic acid | 3300 |
| NaOH | 300 |
| NaHCO$_3$ | 1400 (mg/l) |

In connection with the above RITC 80-7 culture medium, reference is made to I. Yamane et al., Exp. Cell Res., 134, 470(1981).

Figure 5:
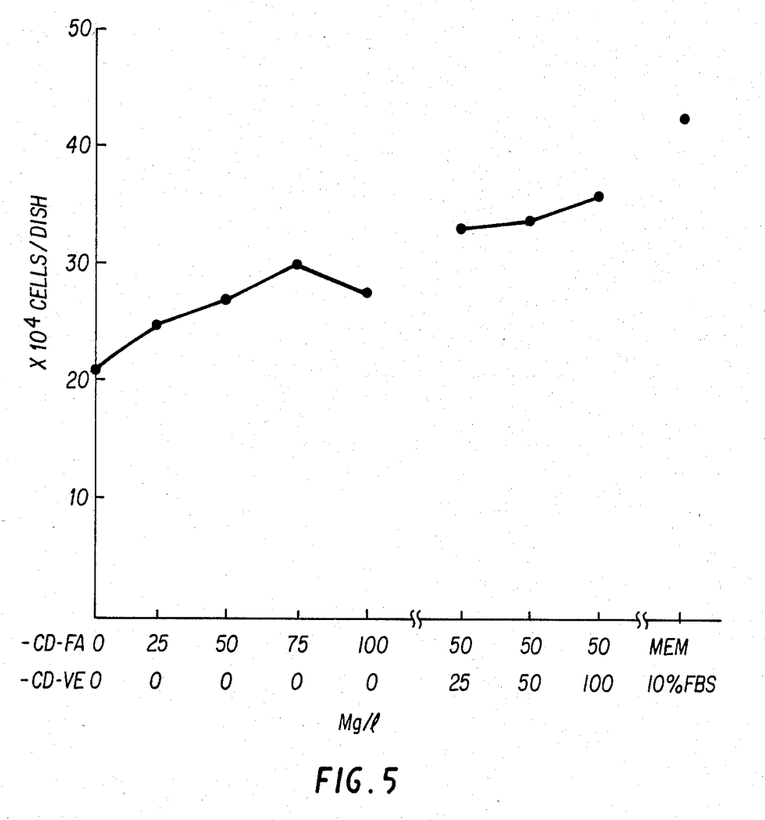

The inclusion complexes given in FIG. 5 of α-cyclodextrin and unsaturated fatty acids or vitamin E prepared by the same method as in EXAMPLE 2 were added in the amounts given in the same figure to RITC 80-7 medium, and the resulting culture medium solution was sterilized by filtration on a membrane filter.

1.5 ml of the sterile medium was pipetted into each 3.5 cm diameter culture dish (Lux Co.). Human embryonic lung diploid fibroblast cells cultured in the MEM medium supplemented with 10 v/v % fetal bovine serum were plated in the above dishes at an initial concentration of $2 \times 10^4$ cells/dish, and cultured at 37° C. for 5 days in air containing 5 vol. % CO$_2$ and 7 vol. % O$_2$.

The results of cell counting in each culture dish are shown in FIG. 5. In this figure, FA means a 1:1 mixture of linoleic acid and oleic acid. As a control examination, the result of cell counting obtained when the same cells were cultured in MEM medium supplemented with 10 v/v % of fetal bovine serum is shown on the right side of the same figure.

EXAMPLE 4

Figure 6:
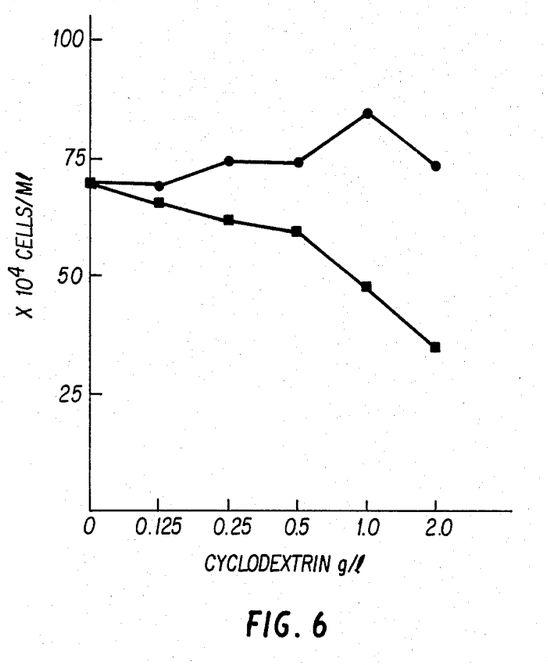

RITC 55-9 culture medium, of which the composition was the same as that of the RITC 56-1 medium except that the former contains no mannose, galactose, lecithin or cholesterol, was added with α- or β-cyclodextrin in the amounts given in FIG. 6 and the resulting solution was sterilized by filtering on a membrane filter.

In order to examine the cytotoxicity of cyclodextrins, UMCL-3 cells were inoculated at an initial cell density of $5 \times 10^5$/ml to RITC 55-9 medium containing various amounts of α- and β- cyclodextrin as shown in FIG. 6, and cultured at 37° C. for 4 days in air containing 5% CO$_2$.

The resulting cell concentrations in the cultured media were measured and are shown against the cyclodextrin concentrations in the same figure. In this figure the closed circles and the closed squares indicate the data obtained in connection with α- and β- cyclodextrin, respectively.

It is evident from the figure that β-cyclodextrin is more toxic than α-cyclodextrin and is more toxic at its higher concentrations.

What is claimed is:

1. In an animal cell culture comprising animal cells and a medium comprising a carbon source, a nucleic acid precursor, amino acids, vitamins, minerals, a lipophilic nutrient, and serum or serum albumin in amounts sufficient to allow the growth of said animal cell culture, an improvement which comprises replacing all serum and serum albumin with α-, β- or γ-cyclodextrin or a mixture of said cyclodextrins.

2. In an animal cell culture medium consisting essentially of a carbon source, nucleic acid precursor, amino acids, vitamins, minerals and a lipophilic substance in amounts sufficient to support the growth of an animal cell or cell line, an improvement wherein said medium further includes (1) serum or serum albumin and (2) an α-, β-, or γ-cyclodextrin or a mixture thereof in amounts sufficient to support said growth, wherein the amount of serum or serum albumin is less than the amount of serum or serum albumin required to support said growth.

3. An animal cell culture which comprises animal cells and a medium comprising a carbon source, a nucleic acid precursor, amino acids, vitamins, minerals, a lipophilic nutrient, and an α-, β-, or γ-cyclodextrin or a mixture of said cyclodextrins in amounts sufficient to allow the growth of said animal cell culture, with the proviso that no serum or serum albumin is present.

4. An animal cell culture medium as set forth in claim 3 in which said lipophilic nutrient and said cyclodextrin together form an inclusion complex.

5. An animal cell culture medium as set forth in claim 3 in which said cyclodextrin is α-cyclodextrin and said lipophilic nutrient is linoleic acid, oleic acid or vitamin E.

6. The animal cell culture medium of claim 3, wherein said lipophilic nutrient is an unsaturated fatty acid, a glyceride of an unsaturated fatty acid, a saturated fatty acid, a glyceride of a saturated fatty acid, or a lipophilic vitamin.

7. The animal cell culture medium of claim 6, wherein said lipophilic nutrient is linoleic acid, linolenic acid, oleic acid, arachidonic acid, erucic acid, palmitic acid, or stearic acid or a glyceride of one or more of said acids.

8. The animal cell culture medium of claim 3, wherein the molar ratio of cyclodextrin to lipophilic nutrient is from 3:1 to 500:1.

9. The animal cell culture medium of claim 3, wherein the molar ratio of cyclodextrin to lipophilic nutrient is from 10:1 to 100:1.

10. The animal cell culture medium of claim 3, wherein said amino acids are selected from the group consisting of L-alanine, L-arginine, L-glutamine, L-methionine, L-threonine, L-lysine, L-valine, and L-phenylalanine, L-cystine, glycine, L-histidine, L-isoleucine, L-leucine, L-serine, L-tryptophan, L-tyrosine, L-asparagine, L-aspartic acid, L-cysteine, L-glutamic acid, and L-proline.

11. The animal cell culture medium of claim 3, wherein said vitamins are selected from the group consisting of ascorbic acid, riboflavin, thiamine.HCl, calcium pantothenate, nicotinic acid amide, pyridoxal hydrochloride, inositol, folic acid, vitamin B$_{12}$, biotin, and folinic acid.

12. The animal cell culture medium of claim 3, wherein said minerals are selected from the group consisting of sodium chloride, potassium chloride, clacium chloride, magnesium sulfate, sodium dihydrogen phosphate, ferrous sulfate, zinc sulfate, sodium selenate, copper sulfate, manganese sulfate, nickel chloride, and ammonium vanadate.

13. The animal cell culture medium of claim 3, which further comprises a metabolic intermediate selected from the group consisting of choline, bitartrate, glutathione, putrescine, sodium pyruvate, lecithin, cholesterol, hypoxanthine, thymidine, deoxycytidine, deoxyadenosine, and 6,8-dihydroxypurine.

14. The animal cell culture medium of claim 3, which further comprises a buffering substance selected from a group consisting of sodium bicarbonate, disodium β-glycerophosphate, and N-2-hydroxyethylpiperazine-N-2-ethane sulfonate.

15. The animal cell culture medium of claim 3, which further comprises insulin, human transferrin, or epidermal growth factor.

16. A method for the preparation of a culture media for the proliferation of mammalian cells which comprises:
(a) reacting a cyclodextrin and a lipophilic substance in a hydrophilic organic solvent to form an inclusion complex of the reaction product of the same;
(b) separating the inclusion complex from the reaction mixture; and
(c) adding the reaction product inclusion complex to an animal culture medium which is free of serum to form a complete animal cell culture medium.

17. A method according to claim 16 wherein the ratio of reactant cyclodextrin to lipophilic substance is from 500:1 to 10:1.

18. A method according to claim 17 wherein the lipophilic substance of the complex is linoleic acid.

19. A method of claim 16 wherein the cyclodextrin-lipophilic substance inclusion complex is introduced in amounts of from 0.1 to 5.0 milligrams per liter of culture medium.

* * * * *